(12) United States Patent
Cheong

(10) Patent No.: US 7,316,249 B2
(45) Date of Patent: Jan. 8, 2008

(54) INFANT FORMULA PREPARATION APPARATUS

(76) Inventor: How Onn Cheong, 54 Harvey Avenue, Singapore (SG) 489526

( * ) Notice: Subject to any disclaimer, the term of this patent is extended or adjusted under 35 U.S.C. 154(b) by 407 days.

(21) Appl. No.: 10/508,723

(22) PCT Filed: May 8, 2002

(86) PCT No.: PCT/SG02/00082

§ 371 (c)(1),
(2), (4) Date: Sep. 20, 2004

(87) PCT Pub. No.: WO03/084377

PCT Pub. Date: Oct. 16, 2003

(65) Prior Publication Data

US 2005/0178799 A1 Aug. 18, 2005

(30) Foreign Application Priority Data

Mar. 20, 2002 (SG) .............................. 200201653-3

(51) Int. Cl.
*B65B 1/04* (2006.01)

(52) U.S. Cl. .................... 141/100; 141/82; 392/442; 392/444; 222/146.5

(58) Field of Classification Search .................. 141/2, 141/18, 9, 100–104, 98, 82; 392/442, 444–451; 222/146.2, 146.5, 129, 129.1, 129.3; 426/402, 426/520, 521, 801; 999/279, 280, 316, 282, 999/299, 290, 283
See application file for complete search history.

(56) References Cited

U.S. PATENT DOCUMENTS

| | | | | |
|---|---|---|---|---|
| 4,595,131 A | * | 6/1986 | Ruskin et al. | 222/640 |
| 6,170,386 B1 | * | 1/2001 | Paul | 99/281 |
| 6,173,117 B1 | * | 1/2001 | Clubb | 392/442 |
| 6,412,527 B1 | * | 7/2002 | Brice | 141/103 |
| 6,766,106 B2 | * | 7/2004 | Roberson | 392/442 |
| 6,951,166 B1 | * | 10/2005 | Sickels | 99/344 |
| 7,048,149 B1 | * | 5/2006 | Lassota | 222/129.3 |
| 7,104,184 B2 | * | 9/2006 | Biderman et al. | 99/282 |
| 7,165,562 B2 | * | 1/2007 | Myong | 134/56 R |

FOREIGN PATENT DOCUMENTS

GB 2 240 465 A * 8/1991

* cited by examiner

*Primary Examiner*—Steven O. Douglas
(74) *Attorney, Agent, or Firm*—Birch, Stewart, Kolasch & Birch, LLP

(57) ABSTRACT

An apparatus for dispensing infant formula including, a steriliser (2) for sterilising a bottle, a milk powder container (4) for dispensing milk powder into the bottle, a water container (3) for dispensing water into the bottle and a controller (8) to control operation of the apparatus.

21 Claims, 2 Drawing Sheets

INFANT FORMULA PREPARATION APPARATUS

FIELD OF THE INVENTION

The present invention is directed towards an apparatus for dispensing infant formula, and in particular an apparatus that is able to contain and mix temperature controlled water with milk powder based on the amount of infant formula desired and ideally is also capable of sterilising bottles prior to dispensing.

BACKGROUND OF THE INVENTION

The number of times a caregiver will have to prepare infant formula for a baby from age 0 to 6 years old is estimated at 8571 times. Of this amount, 6199 times are estimated to be prepared during the day and 2372 times are estimated to be prepared at night. (See table below):

| Age of Infant | Times/Day | Times/Night | Total Times (Day) | Total Times (Night) | Total |
|---|---|---|---|---|---|
| 0 to 6 months | 6 | 2 | 1092 | 365 | 1457 |
| 7 to 12 months | 6 | 1 | 1092 | 182 | 1274 |
| 13 to 24 months | 5 | 1 | 1825 | 365 | 2190 |
| 25 to 36 months | 3 | 1 | 1095 | 365 | 1460 |
| 37 to 48 months | 1 | 1 | 365 | 365 | 730 |
| 49 to 60 months | 1 | 1 | 365 | 365 | 730 |
| 61 to 72 months | 1 | 1 | 365 | 365 | 730 |
| Total | | | 6199 | 2372 | 8571 |

For each feeding, the baby's caregiver is required to take an empty milk bottle properly sterilised and execute the following chores manually;

a) Pour in the required amount of lukewarm water in to the sterilised milk bottle. The caregiver must have a water container to store this lukewarm water;

b) Mix an amount of hot water with this lukewarm water to ensure that this mix of water will be suitable for dissolving the milk formula and ready for feeding;

c) Open up the milk powder container to scoop the required amount of milk powder and place it into the milk bottle with the water at the correct temperature;

d) Thereafter, mix the prescribed amount of milk powder with the warm water.

These chores are often executed by the caregiver with baby in arm and in the dark or with limited lighting. The aim of the caregiver is to execute these chores with precision and in the quickest time so that the baby does not become frantic from crying in hunger. If the baby is promptly fed with milk, the baby is more inclined to sleep again. Otherwise, the baby will be agitated and may not return to sleep readily. This will also impact the caregiver whose sleep will be distorted and insufficient sleep in the long run can affect the health and temperament of the caregiver.

It is essential that the environment where the preparation of infant formula is prepared is convenient and not messy.

To execute the necessary chores efficiently and to ensure that the right mix of hot and warm water to dissolve the milk powder is achieved is not easy. There are many instances where spillage of hot water has resulted in thermal burns to the caregiver, and also spillage of milk powder on to tabletops and the floor creating an unhygienic environment for the baby.

There is also the risk that the final infant formula may not be of the right temperature for feeding and the correct mix of water and milk powder is not often achieved. This lack of consistency in the preparation of infant formula affects the baby's ability to absorb the nutritional value in the infant formula fully, which may result in poor health for the baby in the long term.

Furthermore, the home environment is affected by the presence of so many different containers a) Container for lukewarm water;
b) Container for hot water (normally a thermal flask);
c) Milk powder container;
d) A steriliser for disinfecting the used milk bottle, which must be kept clean and hygienic at all times for the well being of the baby.

Storing all these containers/apparatus in a place away from the baby's room (such as kitchen) will result in numerous trips to and from the baby's room and the kitchen every day and night. The caregiver's chore is further increased by having to re-fill the water containers regularly and ensuring that they are properly sterilised.

Attempts to address the need for water to be at the correct temperature so as to ensure the formula is dissolved properly have been made. Such attempts concentrate on providing an apparatus that provides suitably warm water, however whilst the temperature may be adequate the correct amount of formula may not be added, particularly considering the circumstances in which the mixture is likely to be made.

There is therefore a need for an improved system for ensuring infant formula is prepared efficiently and hygienically.

OBJECT OF THE PRESENT INVENTION

It is therefore an object of the present invention to provide an apparatus that is able to mix and dispense infant formula in an efficient and hygienic manner.

SUMMARY OF THE INVENTION

With the above object in mind the present invention provides an apparatus for dispensing infant formula including:

a steriliser for sterilising said bottle;
a milk powder container for storing milk powder;
a milk powder dispenser for dispensing said milk powder from said container into said bottle;
a water container for storing water;
a water dispenser for dispensing water into said bottle; and
a programmable first controller to control said milk powder and water dispensers, wherein said programmable first controller includes a memory arranged to store data identifying at least one variety of milk powder, and wherein said programmable first controller is arranged to determine a required amount of said milk powder to be dispensed by said milk powder dispenser from:

a) data entered into said memory, said data identifying the stored milk powder, and
b) a required amount of said water to be dispensed by said water dispenser such that the dispensed infant formula contains user required proportions of said milk powder and said water.

Preferably said first controller is arranged to store in the memory a pre-determined set of data identifying a plurality of varieties of said milk powder. More preferably a user may enter additional data into the memory identifying the store milk powder.

The steriliser may include a closeable container and a steam generation means for generating steam to sterilise the bottle. Ideally steam will be generated by heating water in a water reservoir.

The preferred embodiment will be able to sense the water level in the water reservoir and as necessary alert the user to any fault conditions. In such an event the controller should also disable operation of the steriliser.

In the preferred embodiment the milk powder dispenser includes a dispenser which may be motorised and located at the base of the milk powder dispenser so as to dispense predetermined quantities of milk powder into the bottle. The controller should prevent this action if a bottle is not present or insufficient milk powder is in the milk powder container. Ideally the milk powder container is detachable and includes an airtight lid.

The water container should also be preferably detachable, and ideally made of Pyrex or similar stain and heat resistant material. A means of heating the water in the water container should only operate if sufficient water is sensed in the container, and should be able to boil the water.

A water pump can be included to measure desired amounts of water into a bottle, and ideally should only operate if a bottle is present, and sufficient water is in the water container.

The steriliser compartment and dispensing compartment may be separate or combined depending on the preferred configuration.

Whilst the apparatus could be fully automated, it will ideally include a control panel to allow a user to adjust various settings and/or operate the apparatus. This may include adjusting the temperature or dispensing. The control panel preferably includes a graphical display for ease of use, which may take the form of a Liquid Electronic Display or Liquid Crystal Display. The display could include graphical objects and/or text.

DESCRIPTION OF PREFERRED EMBODIMENT

Figure 1:
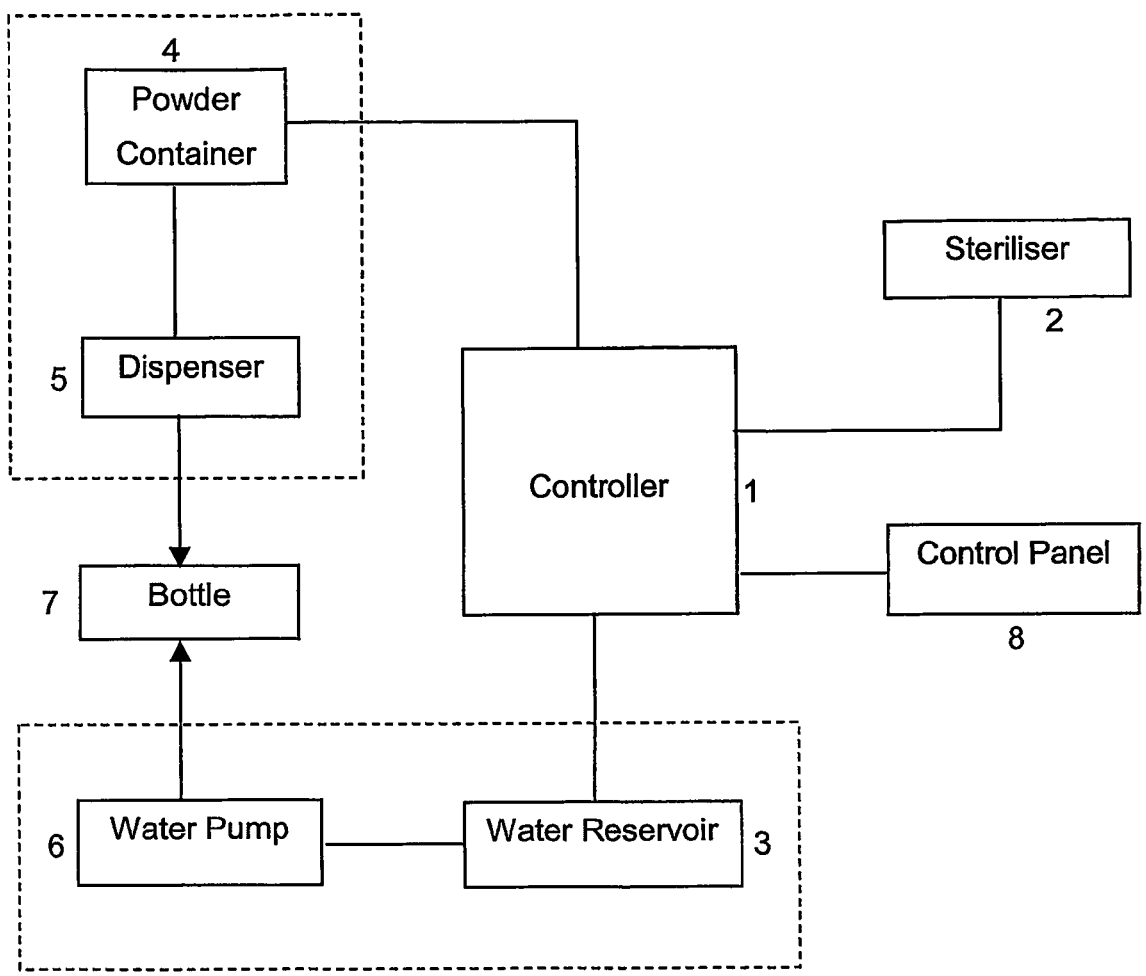
FIG. 1 shows the basic component of the present invention.
Figure 2:
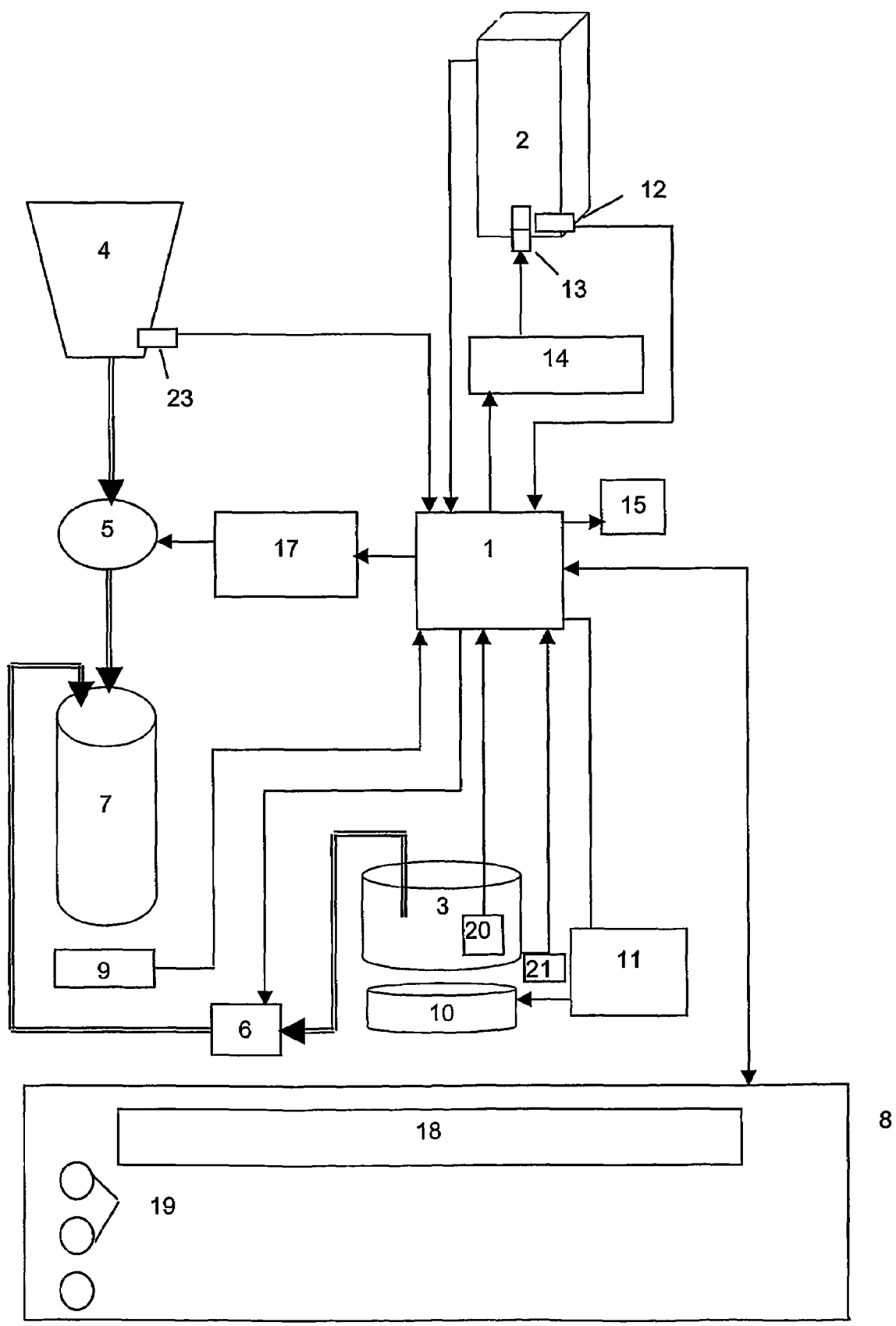
FIG. 2 shows a more detailed layout of a preferred embodiment of the present invention.

The apparatus of the present invention as exemplified in FIG. 1 includes four main functional blocks each connected to a controller 1. These functional blocks, as shown in FIG. 1, include a steriliser 2, a milk powder container 4 and powder dispenser 5, a water reservoir 3 and water dispenser 6, and a control panel 8. Each of these functional components operates to sterilise and efficiently dispense an infant formula into a bottle 7.

The steriliser 2 is a compartment where the empty milk bottle may be kept. There is a small reservoir 22 in the steriliser 2 which the user may fill with water before the sterilising sequence can be initiated. Alternatively, this reservoir 22 may be connected to a water source so that the reservoir 22 may be maintained at an operating level. The preferred embodiment includes a water level sensor 12 that will prevent the initialising of the sterilising sequence if there is no water in the reservoir 22. Similarly, a door switch 16 may be included to again prevent the sterilising sequence being initiated if the door to the sterilising compartment is not closed properly. By preventing sterilisation if the door is partially open, the apparatus prevents steam from escaping into the environment and potentially scalding the user or other persons, and avoids leakage of steam which may prevent the bottles from being sterilised properly.

In order to initiate the sterilising sequence the user may place a bottle in the steriliser 2, ensure that the reservoir 22 is at an adequate level, and the door closed, and then activate the appropriate button 19 on the control panel 8 Alternatively, the device may be configured such that a further sensor detects the presence of a bottle and provided the water level sensor 12 indicates sufficient water is present, and door switch 16 indicates that the door is closed, the steriliser 2 may automatically sterilise the bottle. In a preferred arrangement a further sensor may also sense the amount of content in the milk bottle before any water is dispensed. This helps prevent overflow when the amount of water or infant formula dispensed plus the content also present in the milk bottle before dispensing is more than what the milk bottle can carry, and thus resulting in overflow. In an alternative arrangement, a sensor may also sense the top of the milk bottle and will prevent further dispensing by sending a signal to the controller when the bottle is filled even before the amount of water or infant formula desired by the caregiver is fully dispensed.

The sterilisation process may include the water in the water reservoir 22 being heated by a heater 13 which is controlled by heater controller 14 so as to generate the steam necessary to sterilise the bottle. If the control panel 8 includes a display 18, a message such as "sterilising in progress" may be displayed. The display 18 could take the form of a Liquid Crystal Display (LCD) with two rows of 16 characters. Alternatively, other displays may be utilised.

Once sterilising of the bottle is complete within the programmed time, a buzzer 15 may sound and the display 18 may display a message such as "sterilisation complete". Alternatively a simple LCD may indicate that the sterilisation has been completed.

In a further alternative embodiment the door switch 16 may be connected to a locking mechanism which ensures that the door to the compartment can not be opened until the sterilisation process is completed. In this configuration the device may be adapted such that if the user is unable to open the compartment door, it indicates that sterilisation is in process.

If there are any disruptions to the process, for example the water reservoir 22 falls below a predefined level, or the door is caused to partially or fully open, then the controller 1 would cause the sterilisation process to be suspended or aborted, and an error message can be displayed on the display 18 and/or an audible alarm sounded via the buzzer 15. The device may be configured such that the controller 1 is able to communicate any fault such as insufficient water levels to the user via the display 18 on the control panel 8.

Turning now to the milk powder container 4 this may include a reservoir or compartment within the device. The milk powder container 4 may be used to store infant formula. Infant formula may also be considered to include other milk formula and powdered milk for consumption by adults or the elderly, or powdered food mix for infants and/or adults. The container may be designed to accept standard size packaging, which may be provided by a manufacturer. In the preferred embodiment, the milk powder container 4 includes a detachable plastic container which ideally can hold at least 2.268 kg (2.283 kg multiply by 8 times) of milk powder, as this is considered to be the maximum amount needed by 1 infant/baby for 2 days or 2 infants/babies for 1 day. By being detachable, the container 4 may be more easily cleaned than if the container 4 is fixed within the apparatus. The container 4 should include an airtight lid to prevent any foreign matter from entering into the container 4, and to also keep the milk powder stored in the container 4 fresh.

The preferred apparatus also includes a low level sensor 23 so as to warn the user when the milk powder in the container 4 is at a low level or exhausted. This sensor 23 may detect the weight of the milk powder within the container 4, or alternatively could include an optical sensor or any other means of determining when the milk powder reaches a predetermined level.

Connected to the container 4, and conveniently at the base of the container 4 is a motorised dispenser 5 which is capable of dispensing measured portions of the milk powder. The dispensing action may be controlled by a motor controller 17 attached to the controller 1. The dispenser may include a mechanical door controlled by the controller which opens and shuts accordingly. In this case, the powder in the reservoir will fall due to gravity when the mechanical door is opened.

In one particular embodiment the controller may control the duration for the door to remain open which is dependent on the amount of infant formula required by the caregiver and also the amount of milk powder remaining in the reservoir. The more powder remaining in the reservoir, the heavier will be the weight on the mechanical door and therefore the greater will be volume that fall when the door is opened. Therefore, for the same amount of infant formula needed by the caregiver, the mechanical door will open longer when the powder remaining is less than when the powder remaining in the reservoir is full. The mechanical door may be in the form of a rotary shuttle which opens and shuts when activated. The principle is such as that of the shutter for a camera or the chuck that holds the drill bit in an electric drill. Preferably the mechanical door system provides an airtight seal.

Alternatively, the milk powder dispenser may include a helical or spiral screw type dispenser, for example, an Archimedean screw type device. Thus, the dispensing action may be controlled by a motor controller connected to the first controller whereby the motor controller initiates rotation of the spiral or helical screw to effect dispensing of the milk powder as required by the first controller.

On the preferred apparatus, dispensing of the milk powder would be initiated by the user pressing a button on the control panel which may be marked "dispense". The apparatus will ideally include a sensor 9 to ensure that a bottle 7 is present before any powder is dispensed. Assuming that the milk powder sensor 23 senses sufficient milk powder in the container 4, and the bottle sensor 9 indicates that a milk bottle 7 is present, then when the user elects to dispense the milk powder, the controller 1 will through the motor controller 17 operate the motorised mechanism 5 to dispense the prescribed quantity of milk powder into the bottle 7. The amount of powder dispensed may be calculated based on previous settings either stored in the dispenser or entered by the user. In this way a caregiver could select a prescribed standard concentrate as suggested by a manufacturer or a diluted mixture of the concentrate.

In some embodiments, the user may be able to select the amount of milk powder to be dispensed, and this may include the ability to set the level to zero should the user only wish to dispense water and no milk powder. If such a level is set then the controller 1 should prevent any milk powder from being dispensed, and ideally display a message on the display 18, and or sound and audible alert via the buzzer 15. Similarly, if any error conditions are incurred a similar action should take place. Whilst the powder is being dispensed, the display 18 may indicate the status with a message such as "dispensing powder". In a preferred embodiment, the apparatus will allow the user the flexibility to make infant formula that is less or more concentrated than that specified by milk powder manufacturer. This will cater to the varying need and condition of the infant. By varying the concentration level on, for example, a rotary dial or adjusting the settings in a menu, the user may choose to prepare infant formula that is more or less concentrate than the standard formula. That is, the infant formula may be more or less concentrated than the standard formula. The standard concentration may be specified by milk powder manufacturers and pre-set in the first controller. In one arrangement, the control panel or user interface may consist of the following: a rotary knob for selecting the amount of infant formula needed for each feed, a rotary dial concentric to the rotary knob for selecting the level of concentration of the infant formula needed, 1st button for Dispense/Stop Dispense operations, 2nd button for Boil/Stop boil operations, 3rd button for Sterilise/Stop Sterilise operations, 4th Button for choosing water only, 5th button for choosing powder only, 6th button MENU (SET) i.e. for calibrating, select temperature, on/off sound, choose language, etc, 7th button RESET e.g. to reinstall factory settings after any error, 8th & 9th button for up and down arrow operations.

As for the milk powder container 4, the water reservoir 3 may be formed integrally with the device, and the user simply fills the reservoir 3 as necessary. Alternatively, the water reservoir 3 may be connected to a water source which ensures that the water level within the reservoir 3 is maintained at selected levels. In the preferred arrangement, the water reservoir 3 may be formed by a detachable container preferably made out of food grade Pyrex or some other stain and heat resistant material. It is preferred that the water reservoir 3 would be able to hold capacity for at least eight bottles of which may hold 2.283 kg. By incorporating a detachable container 3, the container 3 may be easily removed to both refill with water and for washing of the container.

A filter means may also be included to filter off unwanted particles from the water before dispensing.

The water storage container 3 will ideally sit on a heater plate 10 which may be controlled by a heater controller 11 connected to the controller 1. It will be appreciated that the heater 10 need not support the water reservoir 3, and that other arrangements may be incorporated provided that the heater 10 is capable of heating the water within the water reservoir 3. For example, a heating element may be arranged to surround the container, or alternatively a heating filament may be inserted into the container.

A sensor 21 may be included to detect the presence of the water reservoir 3, and also the water level within the water reservoir 3. If the sensor 21 indicates that the water reservoir 3 is not present or the water within the reservoir 3 is below a predetermined level, then the controller 1 may prevent the heater 10 from operating. If the water temperature is above or below the desired range suitable for feeding, the controller 1 may also prevent the dispensing of any water or milk powder. Ideally the heater 10 will be controlled using Pulse Width Modulation (PWM) to ensure very accurate control of the water temperature. This temperature may be sensed by a temperature sensor 20 connected to the controller 1.

In an alternative arrangement, the water reservoir 3 may be fixed within the apparatus and effectively sealed from the user. In this arrangement, a water source is connected to the water reservoir 3 to ensure that water within the reservoir 3 is maintained at sufficient levels. Sensors may be incorporated to ensure that the water is maintained above a certain level. Further sensors may be included to ensure that the container is not over filled. In this arrangement the heater 10 may be located within and/or surrounding the reservoir 3 to assist in uniform heating of the water.

In the preferred embodiment, during normal operation the water in the water reservoir 3 is maintained at a temperature which is pre-set or set by the user via the control panel 8. The temperature sensor 20 can take continual readings of the water and relay these to the controller 1. If the controller 1 determines that the water temperature falls below a predetermined temperature, it can activate the heater controller 11 to turn on the heater 10 and thereby raise and maintain the temperature of the water at the desired temperature. Preferably the water will not be continuously re-boiled to preserve a healthy level of mineral and oxygen content. Ideally, the apparatus will include an override switch so as to turn off the heater 10 should the water temperature exceed any predetermined safety level.

The controller 1 should also be configured to disable the heater 10 via the heater controller 11 should a temperature setting be set to zero or off, or any error conditions are present. Ideally, the display 18 would indicate a relevant error or fault message.

Similar to the powder dispenser 5, the water dispenser 6 which may take the form of a water pump will only dispense water from the water reservoir 3 into the bottle 7 if the milk bottle sensor 9 detects that a milk bottle 7 is present. Similarly, if the water level sensor 21 indicates that the level of water in the reservoir 3 is below a predetermined level, the controller 1 will not operate the water pump 6.

Assuming that there are no faults, the controller 1 will operate the water pump 6 to dispense a predetermined amount of water which may be set by the device or controlled by the user via the control panel 8. This could include setting the level to zero should the user only wish to dispense milk powder.

Whilst it is preferred that the water not be constantly re-boiled, in the preferred embodiment, the controller 1 will also ensure that the water pump 6 does not dispense water if the water within the storage container 3 has not been boiled at least once. This ensures that unboiled water is not dispensed into the feeding bottle. Ideally, the controller 1 will also only operate the pump 6 if the temperature sensor 20 indicates that the water temperature is within plus or minus 1° C. of the desired temperature. Whilst this is the preferred error rating, wider temperature variations may be tolerated.

If any faults are detected, then again an audible sound may be made by buzzer 15 and/or displayed on the display 18.

The apparatus may be configured such that when the reservoir sensor 21 senses that the water reservoir 3 has been removed and replaced, and also senses that sufficient water is stored within the reservoir 3, the controller 1 may instruct the heater controller 11 to bring the water to a boil by operating the heater 10. This ensures that the water is boiled at least once. In this arrangement a further embodiment may enable a user to manually override or stop the boiling process in the event that the user is putting in boiled water and no boiling is required. In some embodiments, the user may also be able to select to reboil the water by selecting an appropriate control 19 on the control panel 8. In this situation the controller 1 will again cause the heater controller 11 to operate the heater 10 to boil the water assuming no fault conditions are detected.

The sensor 21 can therefore be installed to detect whenever the water storage container 3 is removed for refilling purposes and then put back. This can then activate the heater 10 to re-boil automatically. In the situation where an external water source is used to maintain the level of water within the reservoir, then the apparatus may be configured to bring the water to the boil whenever water is added via the external source.

Ideally, if the controller 1 detects via the temperature sensor 20 that the temperature of the water has fallen outside a desired temperature range setting, for example 5° C., the heater 10 will again be caused to activate or as necessary deactivate the warming process automatically.

Assuming that the water has been boiled and that no fault conditions exist, the water is dispensed by means of the motorised pump 6 and the volume of water dispensed will depend on predetermined controls or levels set via the control panel.

In some arrangements, the steriliser compartment 2 and dispensing compartment may be separated. In this arrangement the user would initially place the bottle 7 within the steriliser 2 for sterilisation, and once this process is complete remove the bottle 7 from the steriliser 2 and replace it in the dispenser compartment so that the infant formula may be dispensed. Further in a modular construction the steriliser may be designed such that it can be detached from the remainder of the device and still function. In an alternative arrangement, the steriliser 2 and dispenser compartments may be integrated. Water from the water reservoir could be configured to automatically dispense into the sterilising compartment and start the sterilising process, taking away the need to manually pour water to start the process. In this way, the user simply places the bottle 7 within a single compartment. The bottle may then be sterilised, and infant formula dispensed without the necessity of the user to move the bottle from one compartment to a second compartment.

The heater may also be used to maintain the mixed formula at a predetermined temperature. In this way a formula may be premixed and maintained for later use.

The control panel 8 will ideally be user friendly and allow the user to interact with the apparatus. In the preferred embodiment it includes a Liquid Crystal Display having two rows of 16 characters for displaying instructions or messages. It will also ideally include one rotary switch or dial for the user to indicate whether the infant formula is required, or alternatively if only water or milk powder is required. Additional touch buttons may also be included for dispensing infant formula of prescribed Standard concentrate or of a diluted version. Additional touch buttons for water only or milk powder only, to boil or stop boiling, sterilise, calibrate, adjust settings and/or reset. It will be appreciated that varying displays may be used and also varying switches or touch buttons. For example, the temperature setting may be controlled by two touch buttons one for increasing the temperature and one for decreasing the temperature. These buttons may also be used for scrolling up and down any options available to the user which may include calibration. The reset button may be used to enable the apparatus to be brought back to a normal mode following an error or fault detection. It is envisaged that once a fault is detected, that it will be necessary for the user to address the fault and then push the reset button. The system would then perform a check to ensure that the fault was corrected or alternatively simply return the system to a rest status.

The desired apparatus, will be pre-calibrated for use with the 10 to 20 most popular milk powder currently selling in the market. This is to enable the caregiver to easily start using the apparatus by just selecting the type of milk powder they are using. In the event that powder use is not pre-calibrated, the apparatus will preferably include a button to allow the user to manually calibrate the amount of milk powder or water to be dispensed. On selecting of this option, the user could be brought through the calibrating sequence by displaying instructions on the LCD 18.

The apparatus can automatically dispense the right amount of milk powder for the desired amount of infant formula needed. This may be achieved by calibrating the dispenser which involves adjusting an indicator which is linked to the microprocessor in built in the apparatus. As different milk powder has different density, calibrating the dispenser will ensure the right proportion of mix is achieved. Unless the caregiver changes the brand of milk powder, the indicator only needs to be adjusted once.

The apparatus can thus automatically dispense the right amount of milk powder and water, at the right temperature in a one touch operation, for added convenience, and encompasses in just one apparatus, the functions of storing water, storing milk powder, dispensing (milk powder and water) and sterilising a used milk bottle. Thus the milk giver can improve the living ambience, retain more space, reduce hazards of thermal burns and improve the hygiene of the environment.

The present invention therefore provides a device that through a program in a microprocessor can boil and keep water warm at selected temperatures, automatically dispenses the right amount of milk powder and water content in a one-touch operation and sterilises milk bottles and pacifier by producing steam.

The controller 1 is able to centrally control and maintain the water at a desired temperature, and control the amount of milk powder and the amount of water to be dispensed in a virtually "one touch" and "hands free" operation. The microprocessor will, in a preferred embodiment, also through its sensors, indicate and control the water temperature desired and the temperature in the container and the amount of water present in the water compartment and give a warning light/beep when the water level is low and will also give a warning light/beep if milk powder level is low; and all indicators/messages will be displayed on a simple and easy to understand LCD/LED display. Such indicators can be displayed in different languages by programming the microprocessor accordingly. Preferably, when the water temperature is not within a desired temperature range, an indicator light can be caused to light up. When the water temperature has reached the desired temperature range, the same (or another) indicator light may also signal that the water is now at a suitable temperature for dispensing. In an alternative arrangement, the backlight on an LED or LCD display may change depending on whether the desired temperature range is reached.

The microprocessor will further prevent overheating of the water; and dispensing water that is above the desired temperature. Ideally the caregiver will only be able to select within a range of temperature that is deemed safe for dispensing infant formula, to thereby prevent thermal burn of the baby if fed with overheated water. Preferably, the microprocessor will also prevent dispensing water or milk powder when either one of the items is not sufficient for the required feeding thereby preventing the preparation of the infant formula in the wrong proportion; and dispensing of water and powder when the milk bottle is not properly in place, so as to avoid liquid spillage which is hazardous for electrical appliance and wastage of milk powder from occurring. Ideally, the apparatus will also have an adjustable height support to cater to the varying height of milk bottles. The adjustable height support may be manually lifted or lowered to a preselected suitable height and be retained in position by on a friction, gear, spring or motorised operated mechanism.

The microprocessor may also be programmed with factory installed calibration for a number of the most popular milk powders currently selling in the market place. This will make calibration a matter of just making choices. Any milk powder not within the factory-calibrated list can be manually calibrated by following simple programming instructions.

In the preferred embodiment the present invention provides a device with a number of advantageous features including:

a one touch button to automatically dispense the right/desired amount of milk powder for a selected amount of water;

ability to boil and keep water warm at various selected temperatures;

can preferably select between 0.056 kg to 0.283 kg of water for each feeding;

ability to store a reasonable amount of water and milk powder for multiple use;

ability to give warning and prevent dispensing of water if water temperature is not right for feeding;

ability to indicate and give warning if water level or milk powder remaining in the appliance is low;

have luminous indicator lights to assist reading the control panel at night or in low light conditions;

have an indicator to adjust or pre-set the amount of milk powder to dispense for different volume of water required;

have safety features to prevent over heating or short-circuit; This prevents dispensing water that is above the desired temperature. It also ideally has a suction base to prevent dropping off from tabletops;

have energy saving feature; for example auto cut off when the desired temperature is reached or when sterilising is deemed complete after approximately 10 minutes;

it has option to dispense only warm water, instead of both water and milk powder;

it can hold a sterilised milk bottle ready at the spigot/nozzle waiting for the preparation of the infant formula. Therefore it enables virtually "hands free" preparation of infant formula; The caregiver need not hold on to the milk bottle while preparing the infant formula;

it can sterilise and also keep ready mixed infant formula warm at selected temperature.

an airtight hopper to store the milk powder in the apparatus ready for multiple feeding.

It is recognised that future embodiments of the invention may be voice activated to further improve ease of use.

In a preferred arrangement, to prevent the powder dispensing nozzle from clogging due to vapour or humidity, the powder can be dispensed first before the warm water is dispensed. This helps to prevent vapour from the warm water from entering the powder dispensing nozzle. In an alternative arrangement, a very small amount of water may be dispensed first, followed by the milk powder. After the mechanical door for the milk powder dispenser is closed, the remaining amount of warm water will then be dispensed. This helps prevent the milk powder from sticking to the bottom of the milk bottle if milk powder is dispensed first. Preferably the water starts to be dispensed before the milk powder, and then the water continues to be dispensed whilst the milk powder is dispensing, and the water stops being dispensed after the milk powder has finished dispensing. Thus, the likelihood of clogging and/or staining is reduced.

The apparatus will ideally have a removable container in the water heater compartment that uses food grade or other stain resistant materials for easy refilling of water and stain free operation. This is preferred to stainless steel containers, which will gather irremovable chemical composite on its stainless steel wall after a period of time. Such chemical deposits are not healthy for consumption and will drastically alter the mineral content of water and become not suitable for human consumption.

The apparatus will ideally further include an express cooling system for rapidly cooling water that has boiled in the water reservoir back to around body temperature of 37° C. Such a cooling system may be in the form of an electric fan. Alternatively, or in addition, ventilation holes may also be opened near the top of the water reservoir to allow steam and heat to escape easily. This ventilation opening may then be shut when the desired temperature is reached. This helps to prevent dust or particles from entering the water reservoir.

Alternatively, the express cooling system may be in the form of a heat exchanger. For example, a cooling coil through which the heated water is passed to allow heat from the water to pass to the environment. Preferably the heat exchanger includes fan assisted cooling whereby the rate of heat loss from the heat exchanger can be increased to cool the heated water more rapidly than the heat exchanger alone can effect. For example, air can be fan forced over a cooling coil. Preferably the water passing through the heat exchanger may be pump assisted.

In comparison currently available systems only provide warm water at selected temperature. They do not boil water, and attempt to disinfect water using a ultra violet light instead of boiling which is not a proven technology and generally not accepted. Prior systems do not incorporate the milk powder dispensing function and the milk bottle sterilising function. By incorporating all the three main functions of providing warm water, milk powder and sterilising the milk bottle, the present invention ensures hygienic operation at each stage and ensures that the preparation of infant formula is properly mixed and at the correct temperature prescribed, this enables the caregiver to derive the most synergy and efficiency with the least effort and shortest time. Previous systems also do not dispense warm water and milk powder automatically through a one-touch button with settings that are pre-programmed in a microprocessor.

Whilst the method and system of the present invention has been summarised and explained by illustrative examples, it will be appreciated by those skilled in the art that many widely varying embodiments and applications are within the teaching and scope of the present invention, and that the examples presented herein are by way of illustration only and should not be construed as limiting the scope of this invention.

The claims defining the invention are as follows:

1. An apparatus for dispensing infant formula in conjunction with a bottle, comprising:
   a sterilizer for sterilizing said bottle;
   at least one milk powder container for storing milk powder;
   at least one milk powder dispenser for dispensing said milk powder from said container into said bottle;
   a water container for storing water;
   a water dispenser for dispensing water into said bottle; and
   a programmable first controller to control said milk powder and water dispensers;
   wherein said programmable first controller has a memory arranged to store data identifying at least one variety of milk powder; and
   wherein said programmable first controller is arranged to determine a required amount of said milk powder to be dispensed by said milk powder dispenser from:
   a) data entered into said memory, said data identifying the stored milk powder, and
   b) a required amount of said water to be dispensed by said water dispenser
   such that the infant formula to be dispensed has user required proportions of said milk powder and said water.

2. An apparatus according to claim 1, wherein said memory is arranged to store a pre-determined set of said data identifying a plurality of varieties of said milk powder; and
   wherein the amount of milk powder to be dispensed is determined following a user selection from said set of data of the stored variety of milk powder to be dispensed.

3. An apparatus according to claim 1, wherein said memory is arranged to store a non-user predetermined set of said data identifying a plurality of varieties of said milk powder and wherein the amount of milk powder to be dispensed is determined from additional data identifying the stored milk powder entered by a user into the memory.

4. An apparatus according to claim 1, wherein said milk powder dispenser is a motorized dispenser operated by a motor controller enabled by said first controller.

5. An apparatus according to claim 1, wherein said first controller utilizes additional user entered data to determine the concentration of the infant formula above or below a predetermined concentration by adjusting the proportions of selected milk powder to water to be dispensed to give a diluted or enriched infant formula.

6. An apparatus according to claim 1, wherein said sterilizer has a closeable container and a steam generation means for generating steam to sterilize said bottle; and
   wherein said steam generation means has a water reservoir and a first heating means for heating water stored in said reservoir to thereby create steam.

7. An apparatus according to claim 1, wherein said at least one milk powder container has the at least one milk powder dispenser and is detachable.

8. An apparatus according to claim 1, wherein said at least one milk powder container houses the milk powder dispenser.

9. An apparatus according to claim 1, wherein said water container is adapted to be in fluid communication with an external water source or manually filled.

10. An apparatus according to claim 1, further including a second heating means for heating or boiling water in said water container.

11. An apparatus according to claim 10, wherein if water in said water container is at or below a predetermined temperature, said first controller prevents said second heating means from operating.

12. An apparatus according to claim 10, further including a temperature sensor to sense the temperature of water in said water container; and wherein, if the water temperature in said water container falls below a required temperature, said first controller causes said second heating means to heat or boil the water in said water container.

13. An apparatus according to claim 1, further having a control panel, said control panel being connected to said first controller and enabling a user to operate said apparatus.

14. An apparatus according to claim 1, wherein said first controller enables adjustment of water temperature, amount of milk powder dispensed, and/or amount of water dispensed.

15. An apparatus according to claim 1, wherein, the fist controller further enables only water or only milk powder to be dispensed.

16. An apparatus according to claim 1, wherein said first controller enables dispensing, boiling/stop boiling, sterilizing, calibration, setting adjustment and/or reset of the apparatus.

17. An apparatus according to claim 1, wherein said sterilizer is further able to keep warm ready mixed infant formula or breast milk at a desired temperature.

18. An apparatus according to claim 1, wherein said sterilizer is detachable from said apparatus, the detached sterilizer being able to operate independently of said apparatus.

19. An apparatus according to claim 1, wherein said first controller enables a prescribed standard concentrate for each powder variety to be selected and stored in the memory.

20. An apparatus according to claim 1, wherein said programmable first controller is adapted to initiate dispensing of the water before dispensing of the milk powder, and is adapted to stop the dispensing of the water after the required amount of the milk powder has dispensed, thereby ensuring that the milk powder is dissolved and does not stick to the bottle after dispensing.

21. An apparatus for dispensing infant formula including:
a sterilizer for sterilizing a milk bottle;
a milk powder container for storing at least one variety of milk powder;
a milk powder dispenser for dispensing milk powder from said container into the bottle, said milk powder dispenser is a motorized powder dispenser;
a water container for storing water;
a water dispenser for dispensing water into the bottle, said water dispenser is a motorized pump means; and
a programmable first controller to control operation of said motorized powder dispenser and said motorized pump means for adjusting the amount of milk powder dispensed and the amount of water dispensed;
wherein said programmable first controller includes a memory arranged to store data identifying predetermined proportions of the milk powder and the water for at least one variety of milk powder,
wherein said programmable first controller is arranged to determine a required amount of milk powder to be dispensed by said milk powder dispenser from:
a) first data entered into said memory, said first data identifying a specific stored variety of milk powder, and
b) second data entered into said memory, said second data identifying a required amount of the infant formula to be dispensed, such that the dispensed infant formula contains the predetermined proportions of the milk powder and the water, and
wherein said programmable first controller is adapted to initiate dispensing of the water before dispensing of the milk powder, and is adapted to stop the dispensing of the water after the required amount of the milk powder has dispensed, thereby ensuring that the milk powder is dissolved and does not stick to the bottle after dispensing.

* * * * *